United States Patent [19]

Foster

[11] 4,082,092
[45] Apr. 4, 1978

[54] VACUUM CABINET AND GAS VENTING SHIELD

[76] Inventor: Beatrice D. Foster, 21496 H.C.L. Jackson Dr., Grosse Ile, Mich. 48138

[21] Appl. No.: 685,169

[22] Filed: May 11, 1976

[51] Int. Cl.$^2$ ............................................. A61B 19/00
[52] U.S. Cl. .................................. 128/139; 128/1 R; 128/142.7; 128/297
[58] Field of Search ..................... 128/139, 142.7, 188, 128/1 R, 1 B, 142.3, 297, 276; 269/322; 98/115 R, 115 LM; 15/314, 345, 339; 350/63, 236, 241; 240/2 ZM, 2 MA

[56] References Cited

U.S. PATENT DOCUMENTS

| | | | |
|---|---|---|---|
| 1,292,963 | 1/1919 | Replogle | 15/301 |
| 2,210,370 | 8/1940 | Herradera | 95/115 R |
| 2,737,695 | 3/1956 | Sokolik | 128/139 |
| 3,537,447 | 11/1970 | Gauthier et al. | 128/139 |
| 3,565,073 | 2/1971 | Glesy | 128/283 |
| 3,625,207 | 12/1971 | Agnew | 128/139 |
| 3,877,691 | 4/1975 | Foster | 128/132 |

OTHER PUBLICATIONS

"Luminated Micro Magnifier", The Circon Corporation, Santa Barbara, Calif. 93017, Feb. 1, 1973.

*Primary Examiner*—Robert W. Michell
*Assistant Examiner*—Henry S. Layton
*Attorney, Agent, or Firm*—Clarence A. O'Brien; Harvey B. Jacobson

[57] ABSTRACT

A wheeled cabinet is provided and includes a vertically elevatable, universally angularly displaceable and longitudinally extendable boom supported therefrom. The free end of the boom supports a horizontal shield structure defining a shallow downwardly opening cavity and the interior of the cabinet houses a vacuum motor including an inlet and an outlet. A vacuum line is provided and includes an inlet end opening into the interior of the cavity of the shield structure and an outlet end coupled to the inlet of the vacuum motor. Further, an exhaust line is also provided and includes inlet and outlet ends. The inlet end of the exhaust line is coupled to the outlet of the vacuum motor and the outlet end of the exhaust line includes structure for securing the exhaust line outlet end over the register of the inlet for the air circulation exhaust duct for an operating room or the like. The shield structure is transparent and includes a substantially planar portion thereof for viewing therethrough and the planar portion is provided with a magnifier mounted thereon for shifting into and out of predetermined position on the shield structure.

3 Claims, 6 Drawing Figures

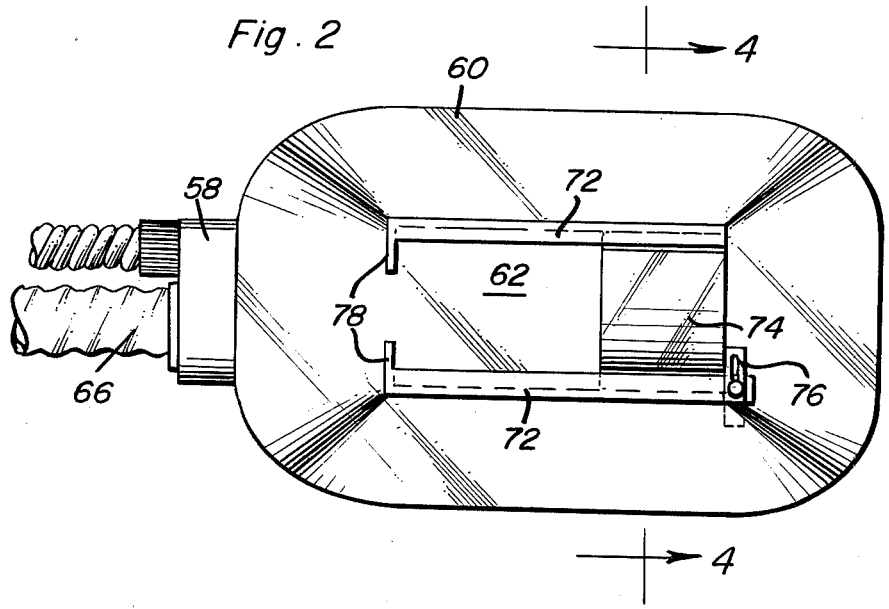
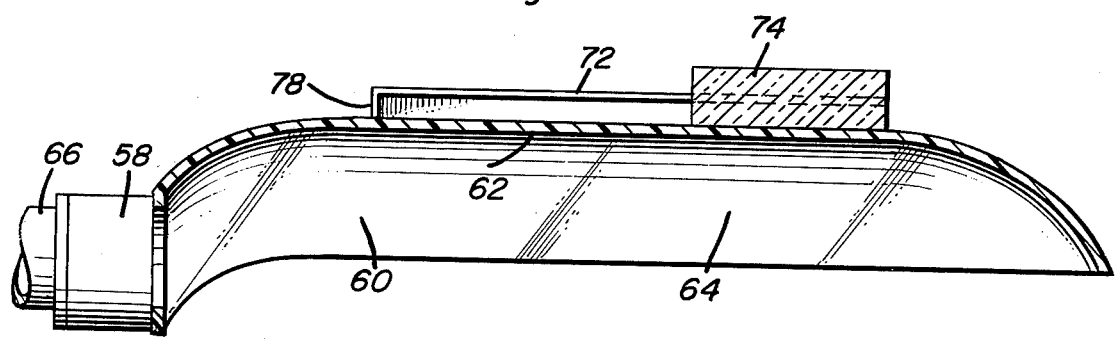
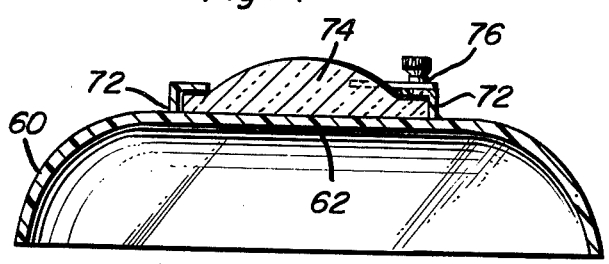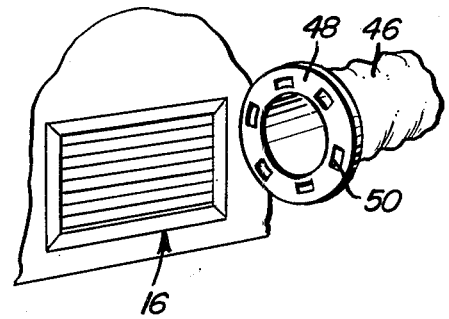

VACUUM CABINET AND GAS VENTING SHIELD

BACKGROUND OF THE INVENTION

The shield of the instant invention may be utilized under various conditions by anesthesiologists while administering anesthesia. Further, the shield may also be used to vent gases rising from incisions in infected body areas.

Although various forms of vacuum devices have been heretofore provided for use in conjunction with surgical procedures and for the purpose of exhausting gases from specified areas, the only gas venting shield of which I am aware and which includes structure and operational features similar to the instant invention is disclosed in my prior U.S. Pat. No. 3,877,691.

BRIEF DESCRIPTION OF THE INVENTION

The shield of the instant invention has been designed as a multi-purpose unit for use by medical doctors and also veterinarians. In addition, the shield, in somewhat modified form, may be used for other purposes such as venting undesirable gases from immediately adjacent an arc or gas welding operation.

The main object of this invention is to provide a transparent shield for diverting and vacuuming off undesirable gases and which includes a planar optically clear portion thereof through which an adjacent work area may be viewed.

Another object of this invention is to provide a shield in accordance with the preceding object and including a magnifier shiftable into and out of predetermined position on the optically clear portion of the shield.

Yet another object of this invention is to provide a shield which will be operative to collect and vent undesirable gases to a remote location.

Yet another object of this invention is to provide a shield which is readily adaptable to enclosed work areas provided with an atmosphere exhausting facility.

Still another object of this invention is to provide a shield constructed in a manner whereby ready access to the associated work area may be afforded at all times.

A final object of this invention to be specifically enumerated herein is to provide a shield in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 2 is a fragmentary enlarged top plan view of the shield;

FIG. 3 is a further enlarged longitudinal vertical sectional view taken substantially upon a plane passing through the longitudinal centerline of the shield;

FIG. 4 is a transverse vertical sectional view taken substantially upon the plane indicated by the section line 4—4 of FIG. 2;

FIG. 5 is a fragmentary perspective view illustrating the outlet end of the exhaust line for the vacuum motor enclosed within the cabinet in position for securement over the register for the air exhaust system of an operating room.

DETAILED DESCRIPTION OF THE INVENTION

Figure 1:
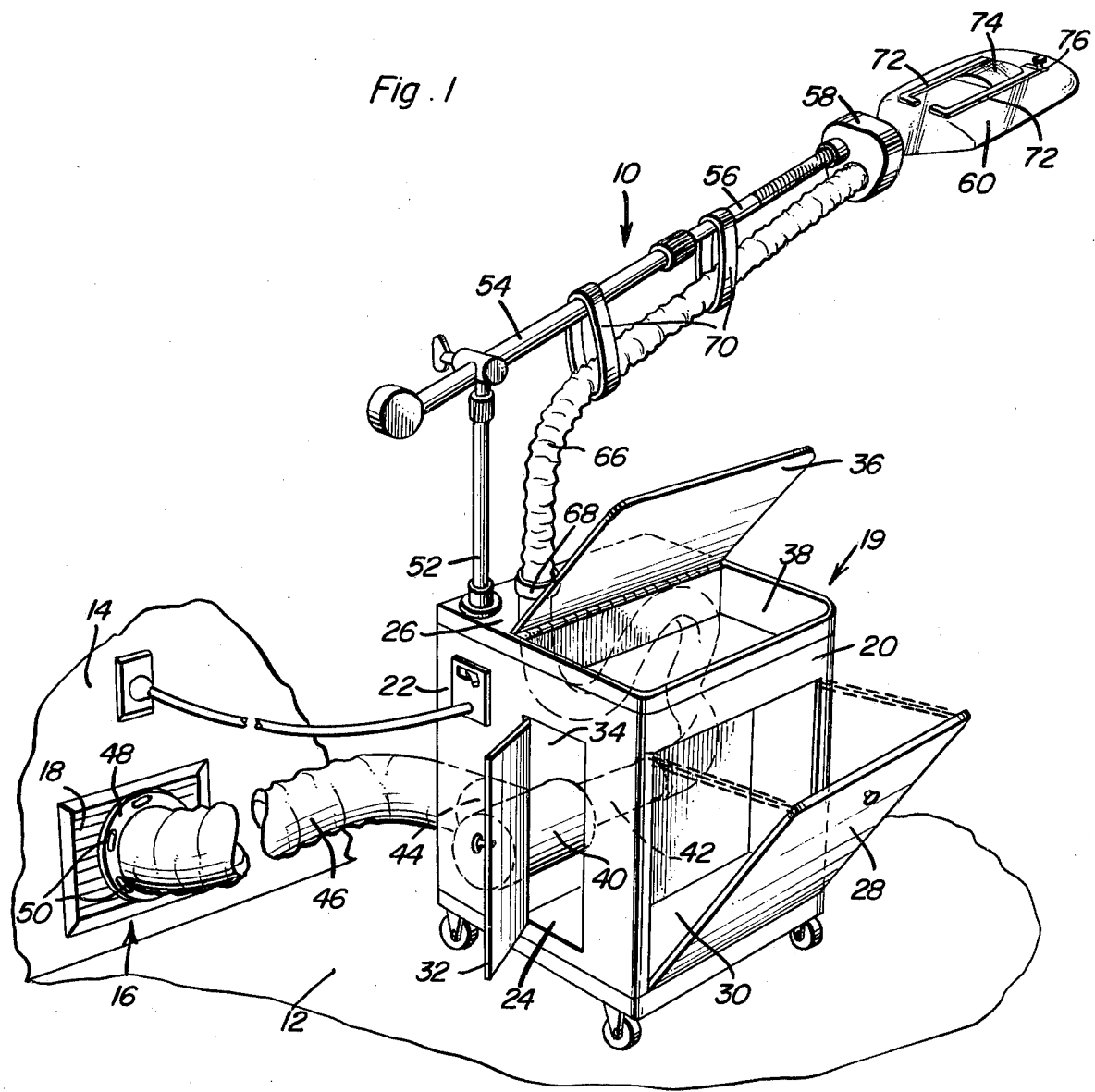
FIG. 1 is a perspective view of the shield operatively associated with a portable cabinet to be used in supporting the shield when the latter is to be used in an operating room.

Referring now more specifically to the drawings, the numeral 10 generally designates the cabinet and gas venting assembly of the instant invention. The assembly 10 is illustrated as supported from the floor 12 of an operating room adjacent one wall 14 of the room into which the inlet end of an air exhaust system referred to in general by the reference numeral 16 opens. A register 18 is secured over the inlet end of the exhaust system 16 and the atmosphere being exhausted from the operating room passes through the openings of the register 18 into the system 16.

The assembly 10 includes an upstanding rectangular cabinet referred to in general by the reference numeral 19. The cabinet 19 includes a plurality of upstanding side walls including a pair of adjacent side walls 20 and 22 and the lower ends of the upstanding side walls are interconnected by means of a bottom wall 24 extending and secured therebetween. Further, the upper ends of the upstanding side walls are interconnected by means of a top wall 26 extending and connected therebetween.

The side wall 20 includes a hinged door 28 closing a first interior compartment 30 within the cabinet 19 and the side wall 22 includes a second hinged door 32 closing a second compartment 34 within the cabinet 19. Still further, the top wall 26 includes a hinged section 36 closing a third upper compartment 38 within the cabinet 19. Of course, the doors 28, 32 and 36 may be swung from the open positions thereof illustrated in FIG. 1 to closed positions closing the associated compartments.

A vacuum motor 40 is housed within the compartment 34 and includes an inlet 42 and an outlet 44. The inlet end of a flexible conduit 46 is connected to the outlet 44 and the outlet end of the conduit 46 has an anchor ring 48 secured thereabout provided with circumferentially spaced magnets 50. The ring 48 may thus be magnetically secured over a portion, only, of the outer side of the register 18 by means of the magnets 50, the register 18 being constructed of ferrous material.

One corner portion of the stationary part of the top wall 26 supports a vertically extendible standard 52 and the upper end of the standard 52 universally supports the counter-balanced base end of a support boom 54. The boom 54 includes an outer longitudinally extendible section 56 which is also angularly displaceable about its longitudinal axis and the free end of the section 56 supports a fitting 58 from which a generally horizontally disposed shield 60 is supported.

The shield 60 is constructed of transparent material and is generally rectangular in plan shape. The shield 60 includes a generally planar transparent center portion 62 and marginal edge portions extending thereabout which curve downwardly toward their free marginal edges in order to define a shallow downwardly opening cavity 64.

A vacuum line 66 comprising a flexible conduit has its inlet end supported from the fitting 58 and opening through the latter into the cavity 64. The outlet end of the vacuum line 66 is connected to the inlet 42 of the vacuum motor 40. An intermediate portion of the vacuum line 66 is slidably received through a sleeve fitting 68 secured through the stationary portion of the top wall 26 adjacent the standard 52 and that portion of the vacuum line 66 extending along the boom 54 is supported therefrom by means of strap loops 70.

The planar portion 62 of the shield 60 includes a pair of parallel longitudinal guides 72 from which a transparent magnifier 74 is supported for longitudinal shifting along the shield 60. One end of one of the guides 72 includes an adjustable stop member 76 which may be moved into and out of position preventing disengagement of the magnifier 74 from the adjacent ends of the guides 72. The ends of the guides 72 remote from the stop member 76 include stationary stop members 78 with which the magnifier 74 is engageable to prevent disengagement of the magnifier 74 from the guides 72.

In operation, the shield 60 may be used in the same manner as the shield disclosed in my prior U.S. Pat. No. 3,877,691. In addition, the shield 60 may be positioned closely over an incision into an infected body area whereby objectional gases from the incision may be vented away from the surgeon and supporting nurses. The magnifier 74 will of course be useful to the surgeon in performing some operations. It is also noted that the assembly 10 may also be used to advantage by veterinarians and the shield 60, when supported from a somewhat different form of standard and boom, may also be used to advantage by other persons such as welders who will find the shield 60 useful in venting objectionable gases from immediately adjacent a welding operation being performed.

In operation, the vacuum motor is actuated and air is drawn into the vacuum line 66 from the cavity 64. The air and gases to be vented therewith are ducted to the inlet 42 of the vacuum motor 40 and thereafter discharged from the outlet 44 into the line 46 for discharging into the system 16 through the register 18. Of course, if the vacuum motor 40 is of the blower type whereby gases may flow therethrough even when the vacuum motor 40 is inoperative, if the system 16 is operative to draw air thereinto through the register 18 from the operating room operation of the vacuum motor 40 may not be needed in all instances. The reduction of air pressure by the system 16 at the outlet end of the line 46 in many cases will be sufficient to cause air to be drawn into the line 66 from the cavity 64.

Figure 6:
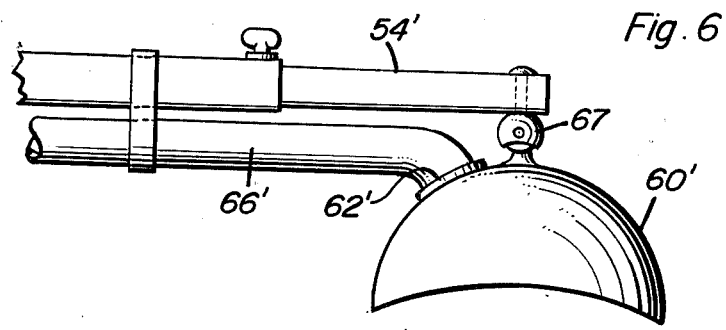
FIG. 6 is a side elevational view of a slightly modified form of shield constructed in accordance with the present invention.

If a planar optically clear portion of the shield 60 such as the portion 62 is not required, the shield 60 may be of partial cylindrical configuration such as the shield 60' illustrated in FIG. 6. Further, the shield 60' has an outlet opening 62' formed therein to which a vacuum line 66' corresponding to the vacuum line 66 may be connected and the shield 60' may be supported from the outer end of a boom 54' similar to the boom 54 by means of a universal socket assembly 67, if desired.

The standard 52 is downwardly retractable into the cabinet 19 and the boom 54 may be dismounted from the upper end of the standard 52 and telescoped into its most compact state and toward within the compartment 30. Further, the fitting 58 and shield 60 may be removed from the boom 54 and connection with the vacuum line 66 and stored in the compartment 38. Also, the line 46 may be disconnected and stored within the compartment 34.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. In combination with an operating room enclosure defined within the confines of upstanding perimeter wall means, a gas diverting shield disposed within said operating room enclosure and comprising a generally horizontal panel structure defining a shallow downwardly opening cavity, a source of vacuum, passage means communicating said source of vacuum with said cavity, a lower portion of said wall means having an exhaust vent opening formed therethrough, said passage means including an outlet end portion registered with a portion, only, of said vent opening, said vent opening comprising the inlet for a blower actuated exhaust system for said operating room enclosure, said vent opening including a ferrous foraminated cover thereover, said outlet end portion of said passage means including magnetic attaching means supported therefrom magnetically attaching said outlet end portion to said cover.

2. The combination of claim 1 wherein said shield includes a substantially planar central section constructed of transparent material, a magnifier mounted on said central section for obtaining a magnified image of objects viewed through said central section, said magnifier being mounted from the upper surface of said central section, said central section and magnifier including coacting means mounting said magnifier for limited shifting across said upper surface into and out of predetermined position on said central section.

3. The combination of claim 1 including a cabinet, a vacuum motor in said cabinet including inlet and exhaust means, said passage means including a first flexible exhaust conduit extending from said exhaust means and having a discharge end, said discharge end comprising said outlet end portion of said passage means, said passage means including a second flexible conduit extending from said shield to said vacuum motor inlet, the first-mentioned flexible conduit having its inlet end connected to said vacuum motor outlet.

* * * * *